United States Patent

Kubalak

Patent Number: 5,312,383
Date of Patent: May 17, 1994

[54] PENILE CATHETER SYSTEM

[75] Inventor: Thomas P. Kubalak, Plymouth, Minn.

[73] Assignee: Mentor Corporation, Minneapolis, Minn.

[21] Appl. No.: 987,204

[22] Filed: Dec. 8, 1992

[51] Int. Cl.⁵ .............................................. A61F 5/44
[52] U.S. Cl. ................................................... 604/350
[58] Field of Search ..................... 604/256, 349–353; 128/844

[56] References Cited

U.S. PATENT DOCUMENTS

| | | | |
|---|---|---|---|
| 4,626,250 | 12/1986 | Schneider | 604/353 |
| 4,713,067 | 12/1987 | Rothenberg et al. | 604/353 |
| 5,087,252 | 2/1992 | Denard | 604/349 |
| 5,102,395 | 4/1992 | Cheer et al. | 604/256 |
| 5,120,316 | 6/1992 | Morales et al. | 604/256 |

Primary Examiner—Randall L. Green
Assistant Examiner—Rob Clarke
Attorney, Agent, or Firm—Hugh D. Jaeger

[57] ABSTRACT

A penile catheter system for urine collection or catheterization where an external catheter secures over the penis and connects to a collection bag through a two-way urine valve, whereby urine can be passed to the collection bag through the two-way urine valve, or whereby catheterization can be accomplished through the two-way urine valve by a catheter with a unique shield that protects the catheter from bacteria laden interior walls of an external catheter. A two-way urine valve can be positioned for urine collection or catheterization as desired.

11 Claims, 4 Drawing Sheets

PENILE CATHETER SYSTEM

CROSS REFERENCES TO CO-PENDING APPLICATIONS

None.

BACKGROUND OF THE INVENTION

1. Field of the Invention—

The present invention pertains to urinary medical devices, and more particularly, relates to a penile catheter system where urine collection or catheterization can be accomplished without removal of any accompanying devices.

2. Description of the Prior Art—

U.S. Pat. No. 4,759,753 discloses an external male urinary catheter having an elastic sheath section which is removably connected to a urine-receiving section. When the device is used as an external catheter, the elastic sheath section (which is adhesively attached to the penile shaft) is coupled to the urine-receiving section in close proximity to the urethral meatus. In the event internal catherization is required, the urine-receiving section is detached from the elastic sheath section, thereby exposing the meatus. The sheath section remains on the penile shaft whether external or internal catherization is employed. Following internal catherization, the urine-receiving section may be reconnected to the sheath section to return the device to the external catheter mode.

SUMMARY OF THE INVENTION

The present invention pertains to a a penile catheter and drainage system. Central to the system is a two-way urine valve, which is connected to an external catheter placed over the penis of a person, such as an incontinent person. Urine, which drains without assistance, passes through an external catheter into a two-way urine valve, which is positioned to port urine through a flexible tube to a collection bag. Should cessation of urine flow by itself occur, the two-way urine valve may be repositioned to cut off the passage bores leading to the collection bag to a position whereby internal bores of the two-way urine valve are aligned so that a sheathed catheter may be introduced through the two-way valve, through the external catheter, and into the urinary tract of the penis for removal of urine by catheterization. A catheter sheath features a collapsible section for manual positioning of the catheter within the sheath.

According to one embodiment of the present invention, there is provided a penile catheter system including an external catheter, a two-way urine valve, a collection bag which connects to a port of the two-way urine valve, a catheter, and a catheter sheath. The two-way urine valve includes a positionable valve core barrel having tubular ports. One vertically oriented port connects to an external penile catheter, a horizontally aligned port connects to a collection bag through a flexible tube and another vertically oriented port accommodates a catheter which passes vertically through the two-way urine valve.

One significant aspect and feature of the present invention is a device having penile catheterization and urine collection capabilities.

Another significant aspect and feature of the present invention is a penile catheterization and urine collection system which allows urine collection or catheterization without the removal of any of the invented devices.

Another significant aspect and feature of the present invention is a two-way urine valve switchable between a urine collection mode and a catheterization mode.

A further significant aspect and feature of the present invention is the alignment of inner bores of the two-way urine valve to allow insertion of a catheter through the two-way valve and into the urethral passage of the penis.

Yet another significant aspect and feature of the present invention is a sheath having elongated holes for access to and manipulation of a contained catheter.

Still another significant aspect and feature of the present invention is an external catheter having a mild adhesive coating the inner circumferential surface.

A further significant aspect and feature of the present invention is an external catheter having a bellows.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
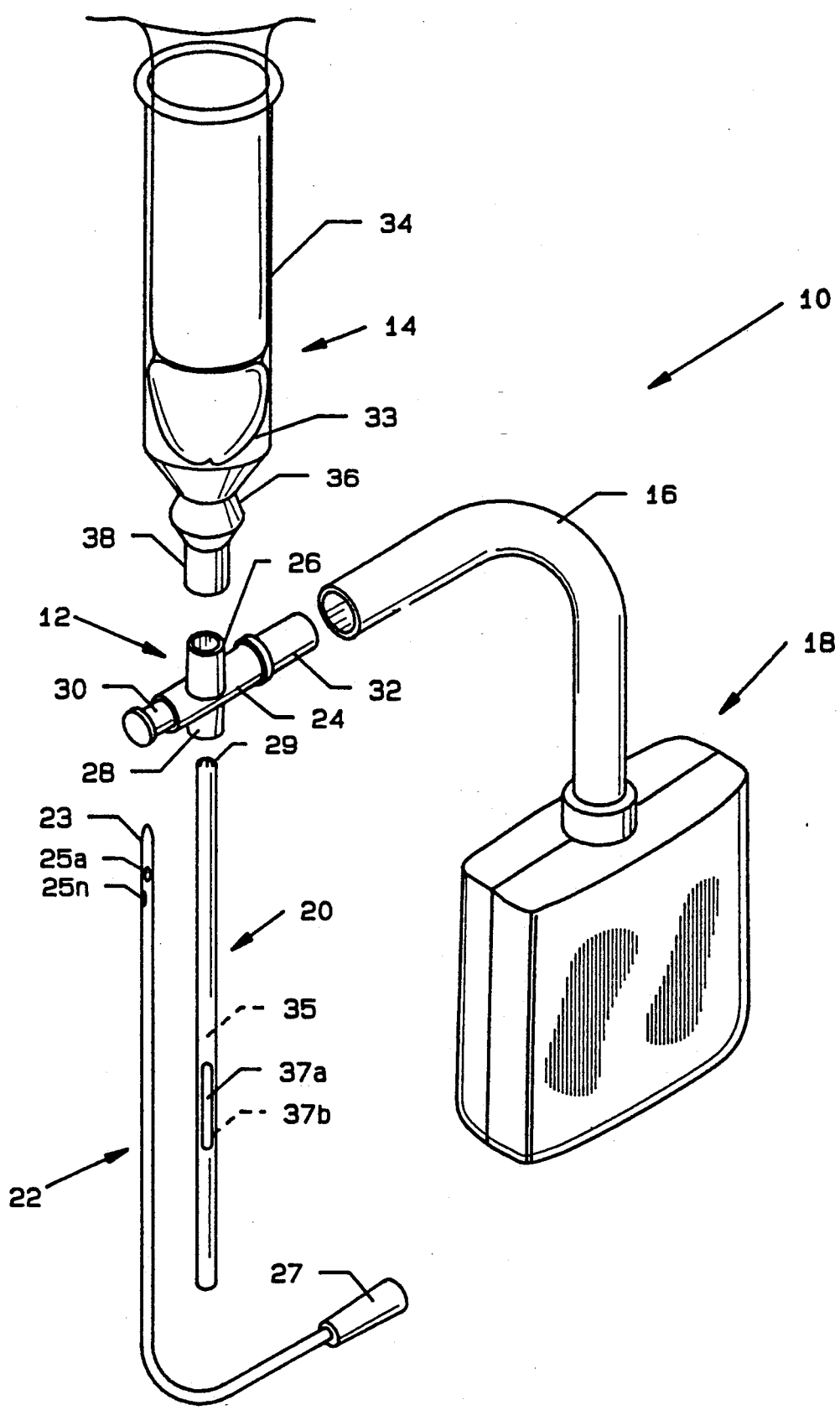
FIG. 1 illustrates a perspective view of the penile catheter and urine collection system.

FIG. 1 illustrates a perspective view of a penile catheter and urine collection system 10 including a two-way urine valve 12, an external condom catheter 14 with a mild adhesive located on its inner circumferential surface, a tube 16 leading from the two-way urine valve 12 to a collection bag 18, a sheath 20, and a catheter 22.

The urine valve 12 includes a tubular main body 24 from which an upper tubular port 26 and a lower tubular port 28 extend. A positionable valve core barrel 30 having a tubular drainage side port 32 at one end aligns within the tubular main body 24. The external catheter 14, for engagement over and about a penis 33, includes an upper and larger radius area 34, a bellow shaped portion 36 and a tubular portion 38. The tubular portion 38 of the external catheter 14 elastically engages the upper tubular port 26 to connect and seal the external catheter 14 to the urine valve 12. The bellows portion 36 allows for non-kinking flexible coupling of the external catheter 14 with the urine valve 12 for ease of handling should perpendicular alignment of the external catheter 14 and the urine valve 12 not be required.

Figure 2:
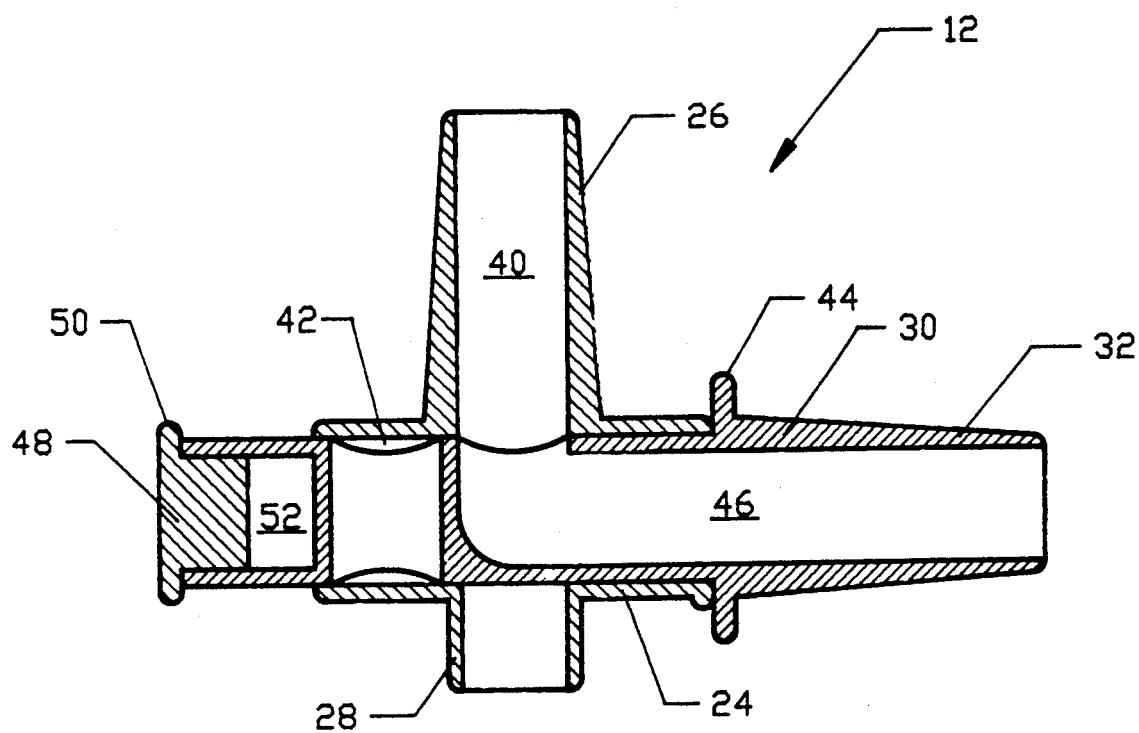
FIG. 2 illustrates a cross-sectional view of the two-way urine valve in the urine drain position.
Figure 3:
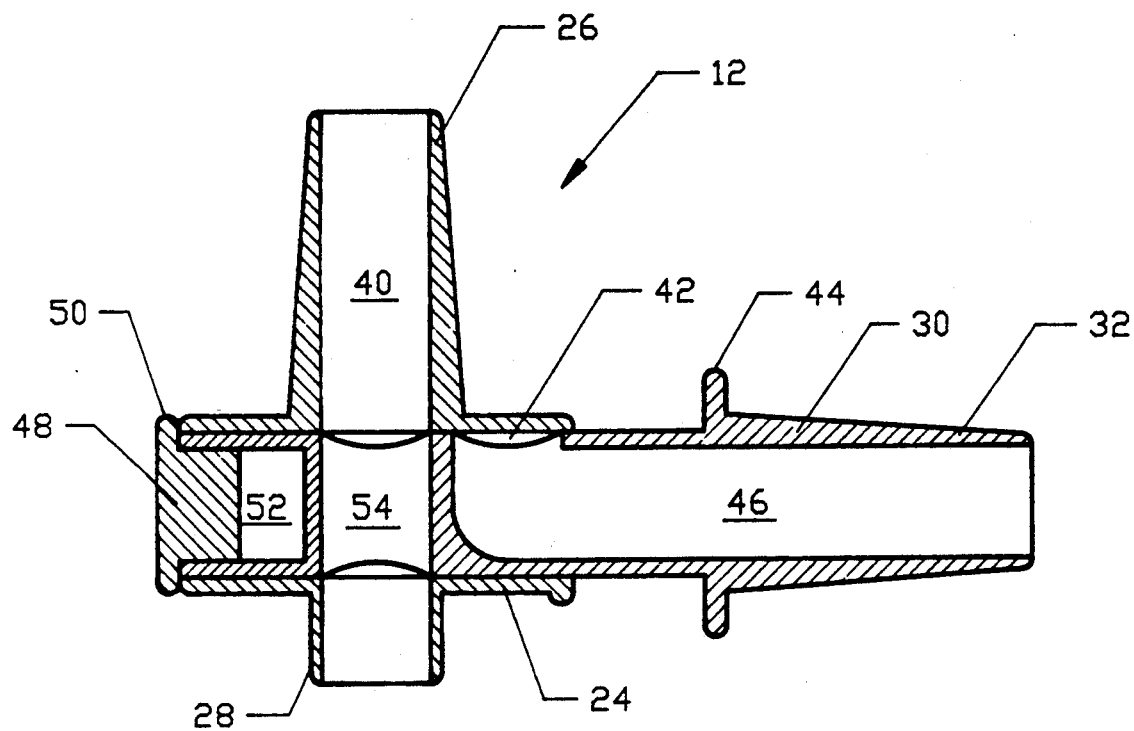
FIG. 3 illustrates a cross-sectional view of the two-way urine valve in the catheterization position; and, FIG. 4 illustrates a cross-sectional view of the catheterization through the two-way urine valve.

The urine valve 12 is positionable between two positions including, as illustrated, the urine drain position, as also illustrated in FIG. 2, and a catheterization position as also illustrated in FIG. 3. One end of the tube 16 elastically engages over and about the tubular side port 32 of the urine valve 12, thus connecting the interior external catheter 14 to the collection bag 18 through the two-way urine valve 12. Fluid flow from the penis 33 flows through the external catheter 14, the two-way valve 12 in the urine drain position, through the tube 16 and into the collection bag 18. Catheterization to produce urine flow may also be accomplished as described in FIG. 4.

The catheter 22 includes a distal tip 23, a plurality of holes 25a–25n connecting to the inner passage of the catheter 22 and an end connector member 27, which can connect to a commode, bed pan, toilet or other such device. The sheath member 20 includes a slitted distal tip 29, an inner passage way 35 and elongated opposing holes 37a and 37b located between the central and lower regions of the sheath 20.

FIG. 2 illustrates cross-sectional view of the two-way urine valve 12 in the urine drain position where all numerals correspond to those elements previously described. A bore 40 extends vertically through the upper tubular port 26, through the main body 24 and finally through the lower tubular port 28. Another bore 42 extends horizontally through the main body 24 for accommodation of the positionable valve core barrel 30. The positionable valve core barrel 30 includes a radial flange 44, which is also a stop, and which limits the travel of the positionable valve core barrel 30 to the left, thus causing proper alignment of an open end bore 46 with the upper bore 40 of the upper tubular port so that urine may be channeled to the collection bag 18 as previously described. A plug 48 with a radial flange 50 aligns in a bore 52 at one end of the positionable valve core barrel 30 and acts as a stop as later described.

FIG. 3 illustrates a cross-sectional view of the two-way urine valve 12 in the catheterization position where all numerals correspond to those elements previously described. The positionable valve core barrel 30 is illustrated in the catheterization position where the positionable valve core barrel 30 has been positioned to its utmost right position to align a vertical bore 54 in the positionable valve core barrel 30 with the vertical bore 40 of the main body 24, thus creating a complete passage through the appropriate vertical bores of the upper tubular port 26, the positionable valve core barrel 30 and the lower tubular port 28 for accommodation of the catheter 22 as described later in detail. The radial flange 50 of the plug 48 acts as a stop, thus limiting travel of the positionable valve core barrel 30, and thereby causing proper alignment of the bores 40 and 54 when the flange 50 contacts the main body 24.

Figure 4:
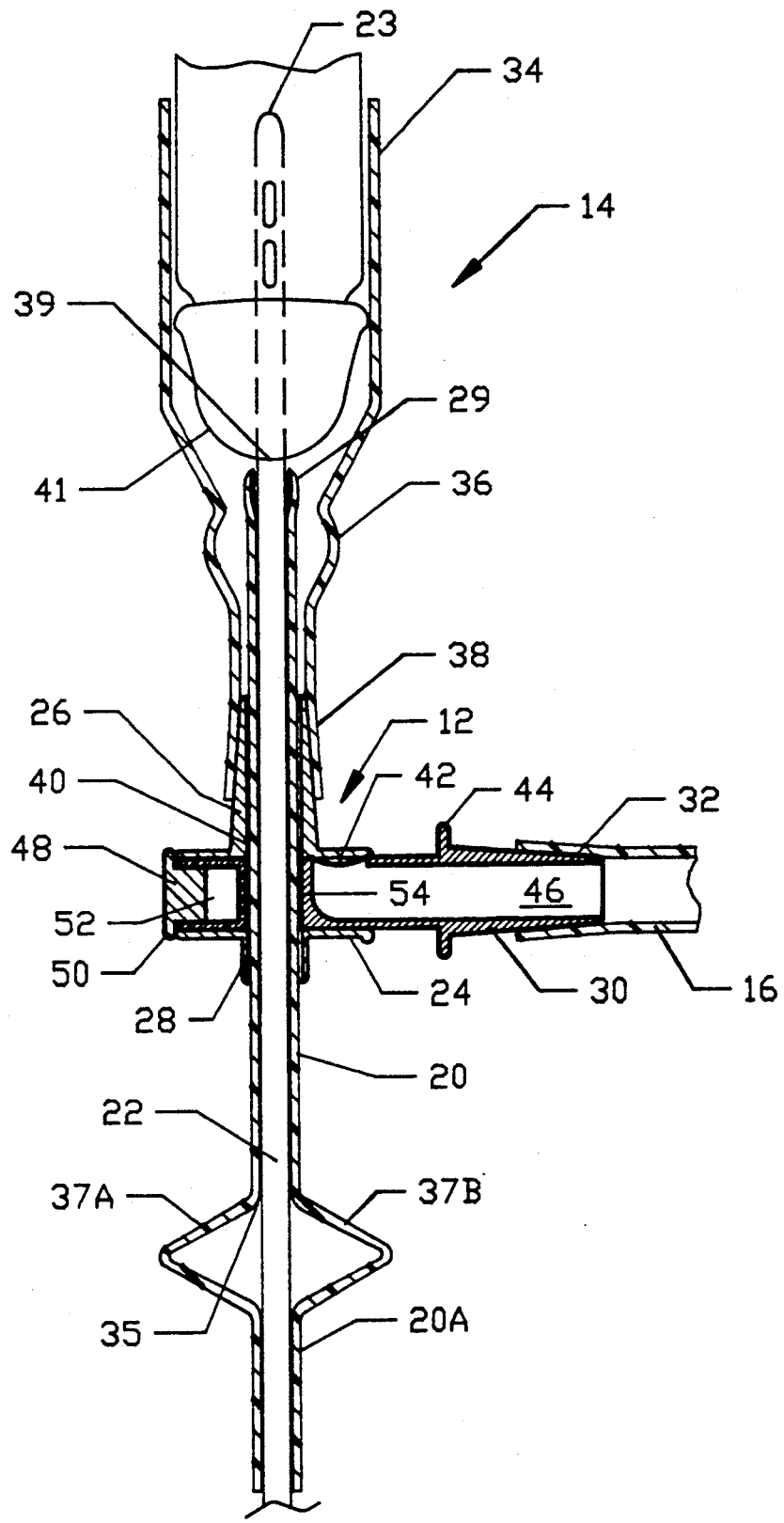

FIG. 4 illustrates catheterization through the two-way urine valve 12 where all numerals correspond to those elements previously described. For catheterization, the positionable valve core barrel 30 is positioned to its right most position, thus aligning the vertical bores 40 and 54 as described in FIG. 3. The catheter 22 is first inserted fully into the sheath 20, bringing the distal tip 23 in very close proximity to the slitted tip 29 of the sheath 20. The combined sheath 20 and catheter 22 are then inserted through the lower tubular port 28 and through the aligned vertical bores 40 and 54 and through the upper tubular port 26 to a position adjacent to the urethral meatus 39 at the glans penis 41. Upward force is then manually exerted upon the lower portion 20a of the sheath 20 with one hand causing the portion of the sheath adjacent to the elongated holes 37a and 37b to bend outwardly as illustrated, thus pushing the catheter 22 through the slitted end 29 of the sheath 20 and into the urethral meatus 39 for catheterization as illustrated.

Various modifications can be made the present invention without departing from the apparent scope hereof.

I claim:

1. A penile catheter system, comprising:
   a. a condom portion dimensioned to be fitted on and extend along the shaft of the penis;
   b. urine valve means in fluid communication with said condom portion, said urine valve means having a first port and a second port and means for allowing fluid flow to only one of said ports at any one given time; and,
   c. a portion of said condom portion engages about said penis and terminates in a bellows portion extending beyond said penis, said bellows portion terminating in a tubular portion dimensioned so as to receive said urine valve means.

2. The penile catheter system of claim 1, further comprising a urine collection receptacle in fluid communication with said first port of said urine valve means.

3. The penile catheter system of claim 1, further comprising an internal catheter and outer catheter sheath dimensioned to be inserted into said second port, said condom portion, and said penis.

4. A penile catheter system, comprising:
   a. a condom portion dimensioned to be fitted on and extend along the shaft of a penis;
   b. urine valve means in fluid communication with said condom portion, said urine valve means having a first port and a second port and means for allowing fluid flow to only one of said ports at any one given time;
   c. an anti-bacteria sheath for the protection and advancement of a urethra penetrating catheter for the purpose of draining urine from the bladder; and,
   d. a portion of said condom portion engages about said penis and terminates in a bellows portion extending beyond said penis, said bellows portion terminating in a tubular portion dimensioned so as to receive said urine valve means.

5. The penile catheter system of claim 4, further comprising a urine collection receptacle in fluid communication with said first port of said urine valve means.

6. The penile catheter system of claim 4, further comprising an internal catheter and outer catheter sheath dimensioned to be inserted into said second port, said condom portion, and said penis.

7. A penile catheter system comprising:
   a. a condom portion dimensioned to be fitted on and extend along the shaft of a penis;
   b. a two-way valve connected to said condom portion, said two-way valve having a barrel with a first bore and a second bore, said first bore allowing fluid communication between said condom portion and a urine collection receptacle, said second bore allowing insertion therethrough of an internal catheter;
   c. said two-way valve has a first tubular portion dimensioned to connect with said condom portion, and a second tubular portion housing said barrel; and,
   d. wherein said barrel is moveable in said second tubular portion from a first position allowing fluid communication between said condom portion and said urine collection receptacle, and a second position preventing fluid communication between said condom portion and said urine collection receptacle.

8. The penile catheter system of claim 7, wherein said second position of said barrel allows insertion of said internal catheter through said first tubular portion of said valve.

9. A penile catheter system comprising:
   a. a condom portion dimensioned to be fitted on and extend along the shaft of a penis;
   b. a two-way connected to said condom portion, said two-way valve having a barrel with a first bore and a second bore, said first bore allowing fluid communication between said condom portion and a urine collection receptacle, said second bore allowing insertion therethrough of n internal catheter; and,
   c. a portion of said condom portion engages about said penis and terminates in a bellows portion extending beyond said penis, said bellows portion terminating in a tubular portion dimensioned so as to receive said two-way valve.

10. A process for converting an external penile catheter into an internal penile catheter, comprising:
    a. providing a condom portion for engagement about a penis; and,
    b. switching a two-way valve in fluid communication with said condom portion and said penis from an external catheter mode which allows fluid communication between said condom portion and a urine collection receptacle, to an internal catheter mode which prevents fluid from communicating from said condom portion to said urine collection receptacle and opens a passageway in said two-way valve allowing for insertion of an internal catheter into said penis.

11. The process of claim 10, wherein said two-way valve comprises:
    a. a first tubular portion dimensioned to connect with said condom portion, and a second tubular portion housing a barrel having a first bore and a second bore;
    b. said first bore providing in said external catheter mode fluid communication between said condom portion and said urine collection receptacle;
    c. said second bore allowing in said internal catheter mode insertion therethrough of said internal catheter; and,
    d. wherein said switching step comprises moving said barrel in said two-way valve from said external catheter mode to said internal catheter mode.

* * * * *